United States Patent [19]

Orsolini et al.

[11] Patent Number: 5,439,688

[45] Date of Patent: * Aug. 8, 1995

[54] PROCESS FOR PREPARING A PHARMACEUTICAL COMPOSITION

[75] Inventors: Piero Orsolini, Martigny; Frédéric Heimgartner, Villeneuve, both of Switzerland

[73] Assignee: Debio Recherche Pharmaceutique S.A., Martigny, Switzerland

[ * ] Notice: The portion of the term of this patent subsequent to Jul. 6, 2010 has been disclaimed.

[21] Appl. No.: 790,033

[22] Filed: Nov. 12, 1991

Related U.S. Application Data

[63] Continuation-in-part of Ser. No. 555,973, Jul. 20, 1990, Pat. No. 5,134,122.

[30] Foreign Application Priority Data

Nov. 14, 1990 [CH] Switzerland .................. 03616/90

[51] Int. Cl.⁶ .................. A61K 9/14; A61K 37/24; A61K 9/48
[52] U.S. Cl. .................. 424/489; 424/423; 424/426; 424/451; 424/497; 424/501; 424/502; 514/800; 514/806; 514/808; 514/963; 930/21; 930/130; 930/160
[58] Field of Search .................. 424/422–429, 424/484, 486, 489, 497, 498, 78.08, 451, 501, 502; 514/2, 15, 724, 785, 800, 806, 808, 963; 530/307, 311, 313, 817; 930/21, 130, 160; 428/402.21

[56] References Cited

U.S. PATENT DOCUMENTS

| | | | |
|---|---|---|---|
| 4,010,125 | 3/1977 | Schally et al. | 260/8 |
| 4,107,288 | 8/1978 | Oppenheimer et al. | 424/489 |
| 4,349,530 | 9/1982 | Royer | 424/489 |
| 4,483,807 | 11/1984 | Asano et al. | 264/22 |
| 4,622,244 | 11/1986 | Lapka et al. | 427/213.32 |
| 4,675,189 | 6/1987 | Kent et al. | 424/490 |
| 4,767,628 | 8/1988 | Hutchison | 424/426 |
| 4,835,139 | 5/1989 | Tice et al. | 514/15 |
| 5,055,300 | 10/1991 | Gupta | 424/489 |
| 5,100,669 | 3/1992 | Hyon et al. | 424/497 |
| 5,187,150 | 2/1993 | Speiser et al. | 514/2 |
| 5,225,205 | 7/1993 | Orsolini | 424/489 |

FOREIGN PATENT DOCUMENTS

| | | |
|---|---|---|
| 52510 | 6/1982 | European Pat. Off. . |
| 58481 | 8/1982 | European Pat. Off. . |
| 204476 | 12/1986 | European Pat. Off. . |
| 0211267 | 2/1987 | European Pat. Off. . |
| 251476 | 1/1988 | European Pat. Off. . |
| 302582 | 2/1989 | European Pat. Off. . |
| 311065 | 4/1989 | European Pat. Off. . |
| 60-181029 | 9/1985 | Japan . |
| 2209937 | 9/1989 | United Kingdom . |

OTHER PUBLICATIONS

Chang, "Biodegradable Semipermeable Microcapsules Containing Enzymes, Hormones, Vaccines and Other Biologicals", J. Bioeng. 1 (1976) p. 25.

Langer, "Controlled Release of Macromolecules", Chemtech Feb. 1982, pp. 98–105.

Hutchison et al., "Biodegradable Carriers for the Sustained Release of Polypeptides" TIBTECH, Apr. 1987 (vol. 5), pp. 102–106.

M. Mason-Garcia et al., "Radioimmunoassay for Octapeptide Analogs of Somatostatin," Proc. Nat'l. Acad. Sci., vol. 85, pp. 5688–5692 (1988).

Fraser et al., "An implant of a gonadotropin releasing hormone agonist (buserelin) which supresses ovarian function in the macaque for 3–5 months", Acta Endocrinol. (Copenhagen), 115(4), 521–7 (1987).

Primary Examiner—Thurman K. Page
Assistant Examiner—Carlos Azpuru
Attorney, Agent, or Firm—Pennie & Edmonds

[57] ABSTRACT

A pharmaceutical composition is prepared in the form of microparticles or of an implant comprising a biodegradable polymer selected from poly-1,4-butylene succinate, poly-2,3-butylene succinate, poly-1,4-butylene fumarate and poly-2,3-butylene succinate, incorporating as the active substance the pamoate, tannate, stearate or palmitate of a natural or of a synthetic peptide comprising 3 to 45 amino acids, such as LH-RH, somatostatin, GH-RH or calcitonin, or one of their synthetic analogues or homologues. The preparation comprises dry blending the ingredients in the form of powders, pre-compressing and preheating the mixture and then extruding the pre-compressed and pre-heated mixture. The product resulting from the extrusion step can then be comminuted and finally sieved.

24 Claims, No Drawings

PROCESS FOR PREPARING A PHARMACEUTICAL COMPOSITION

This is a continuation-in-part of application Ser. No. 07/555,973, filed Jul. 20, 1990, and now U.S. Pat. No. 5,134,122.

The object of the invention is a process for preparing a pharmaceutical composition, in the form of microparticles or of an implant, the composition thus obtained and its use.

More specifically, the object of the invention is a process for preparing a pharmaceutical composition designed to ensure a sustained and a controlled release of a drug, comprising a biodegradable copolymer of the polyester type, such as a polysuccinate or a polyfumarate and incorporating as the active substance, the pamoate, tannate, stearate or palmitate of a natural or of a synthetic peptide, and more particularly, of a peptide comprising 3 to 45 amino acids.

Various solutions have been proposed to this day for preparing compositions ensuring the sustained and the controlled release of drugs, which make use of biodegradable implants, microencapsulation or biodegradable porous matrices which are obtained for example as microparticles of various sizes. One can mention in this respect, EP-A-0052510 for micro-encapsulation, EP-A-0058481 or U.S. Pat. No. 3,976,071 for the preparation of implants or biodegradable porous matrices based substantially on a polylactide or a co-poly-lactide-glycolide, or further DE-A-3835099.8, which is concerned with polyesters such as for example poly-1,4-butylene succinate or fumarate, and poly-2,3-butylene succinate or fumarate. All these techniques involve first dissolving the biodegradable polymer or copolymer used as support in an organic solvent, and sometimes dissolving also the drug itself. If in such cases, the dispersion of the active substance through the bulk of the biodegradable polymer is satisfactory, the problem still remains that trace amounts of solvent are retained which can jeopardize the use of such compositions in therapeutic applications. Choosing low toxicity solvents or thoroughly removing trace amounts of residual solvent can be sometimes complicated and costly, and it can further result in an unacceptable loss of purity for the product.

It has also been proposed to dry blend—i.e. mix without using any solvent powers of—a proteinic substance (Bovine Serum Albumine) and a biodegradable copolymer of lactic and glycolic acid, and then to proceed to the compression of the mixture at its melting temperature (J. D. Gresser and col., Biopolymeric Controlled Release System Vol. II, p. 136). This technique has not proven satisfactory, in particular for achieving a homogeneous distribution of the proteinic substance (BSA) throughout the bulk of the product and accordingly, for ensuring the regularity of the release of the active substance.

Against all expectations, it was found that these various difficulties could be overcome according to the process of the invention by using biodegradable polymers selected from poly-1,4-butylene succinate, poly-2,3-butylene succinate, poly-1,4-butylene fumarate or poly-2,3-butylene fumarate, natural or synthetic peptides such as octa-, nona-, or decapeptides, and more generally peptides comprising 3 to 45 amino acids are the active substances which are incorporated into these polymers according to the process of the invention, and which are subsequently released from the polymers in a controlled manner. Poly-1,4-butylene succinate is the preferred polymer.

According to the invention, natural or synthetic peptides are used in the form of their salts, and more particularly as pamoates, tannates, stearates or palmitates, and preferably as pamoates. It should be noted at this point, that these peptide salts are water-insoluble.

Both the above-mentioned salts and the above-mentioned biodegradable polyesters are used as powders, and more particularly as microparticles having an average size smaller than about 500 microns. Good results were achieved with polymeric microparticles in the order of 180 microns or less, and the particle size of the peptide salt can be even smaller. The mixture of these compounds is carried out by dry blending in any appropriate equipment, such as for example a ball mill, at room temperature.(about 25° C.) or even at a lower temperature, for example in the range from 5° to 10° C. The proportions of the powdered components can vary considerably, depending on the therapeutic effect desired, for example from 0.1 to 15% in weight for the peptide salt.

According to the invention, once the selected mixture is thoroughly homogenized, it is subjected to a progressive compression and, simultaneously, to a progressive heating before being extruded. Both operations, as well as the transfer of the mixture to the pre-compression and pre-heating zone can be advantageously carried out using an appropriately dimensioned endless screw or, if required, two co-operating endless screws. The compression rate can vary depending on numerous factors such as extruder geometry or particle size of the powdered mixture. An important factor which must be controlled is the pre-heating and its evolution as the mixture moves forward; depending upon the nature of the products to be treated (polyester, peptide), one should strive to maintain a temperature gradient with a maximum of about 90° C. The initial temperature of the powdered mixture can be 25° C., or it can be higher or lower, depending on the characteristics of the substances involved.

The mixture thus pre-compressed and pre-heated is then subjected to an extrusion at a temperature between approximately 90° and 100° C., the upper limit of this range being function of the nature of the drug (peptide), which must not be allowed to deteriorate. The extrusion can be carried out at a wide range of pressures extending from 50 to 500 kg/cm$^2$, the important point being that the extrusion temperature and the pressure must be suited to the viscosity of the product. The appropriate pressure and temperature are important in order to ensure the perfect homogenization of the ingredients and in particular the regular distribution of the peptide salt throughout the bulk of the biodegradable polymer.

The extrusion per se is carried out using a die of conventional shape and size, which is located at the downstream end of the above-mentioned endless screw. The cooling of the extruded product is ensured by any appropriate means, for example through a simple heat transfer to cooled sterile gas or air.

When the process of preparation is stopped after this step, a composition in accordance with the invention is obtained in the form of implants. Such implants are simply collected by cutting segments of predetermined length as the product is pressed out from the extrusion die.

Incidently, the shape of said implants can be varied by changing the shape of the extrusion die.

In one embodiment of the invention, the extruded product appropriately cooled is subsequently comminuted at decreased temperature, preferably at a temperature below 0° C., or even much lower, such as for example −30° C. Cryogenic comminution, a technique which is known per se, is advantageously used for this purpose. In accordance with the process of the invention, the product thus comminuted is then subjected to a selection of microparticles based on their average size, with particles smaller than 200 microns and preferably smaller or equal to 180 microns being retained. This selection of microparticles can be carried out for example, by sieving. The microparticles thus selected and collected are ready for use.

In accordance with the process of the invention, the above-described steps are carried out in succession without any excessive time lag between steps. The advantage of this process is that it can be carried out on a continuous basis, with all the operations being carried out one after the other, merely by transferring the mixture being processed.

According to the invention, a biodegradable polyester comprised of poly-1,4-butylene succinate is the preferred biodegradable polymer. Such polymers are easily prepared as described in the cited literature and they can be obtained commercially from specialized firms.

Whether they be natural or synthetic, the peptide salts incorporated into the polymer are preferably peptide salts comprising 3 to 45 amino acids, and more particularly salts of LH-RH (Luteinizing Hormone—Releasing Hormone), somatostatin, GH-RH (Growth Hormone—Releasing Hormone), calcitonin or of their synthetic homologues and analogues.

More particularly, the products are chosen amongst the pamoates of LH-RH, somatostatin or of synthetic homologues and analogues thereof, such as first milled at a decreased temperature and sieved to obtain microparticles with an average size of 500 microns or less.

To this powdered composition, 0.445 g of finely comminuted D-Trp$^6$-LH-RH pamoate were added, the peptide having the following formula: (pyro)Glu-His-Trp-Ser-Tyr-D-Trp-Leu-Arg-Pro-GIY-NH$_2$.

This product consists of microparticles of about 10 microns and its structure is amorphous. The resulting mixture was homogenized at room temperature, using a mill.

The resulting homogenized mixture was then placed inside an apparatus equipped with an endless screw cooperating with a conventional extrusion die. The endless screw can have a length of about 25 cm and a diameter of about 1.5 cm. It comprises a first zone which functions simply to move the mixture and which is adjacent to a second zone, designed for the compression and the pre-heating.

As it moves forward, the mixture is heated from 25° to about 90° C., the rate of progression being selected so that this phase lasts about 5 min. The extrusion per se takes place at 98° C., through an extrusion die with an orifice having a diameter of about 1.0 mm.

The filaments thus obtained are allowed to cool to room temperature, then they are cut into small segments and finally milled at −30° C. After sieving, those microparticles having an average diameter of 180 microns or less are collected.

The chemical analysis carried out on samples of the product after extrusion and milling confirms the perfect homogeneity of the dispersion of the active substance throughout the bulk of the polymer.

The microparticles obtained above were subjected to a sterilization by gamma rays and then they were suspended in an appropriate sterile vehicle.

The in vivo tests (determination of the blood testosterone level in strains of male rats) confirm that the

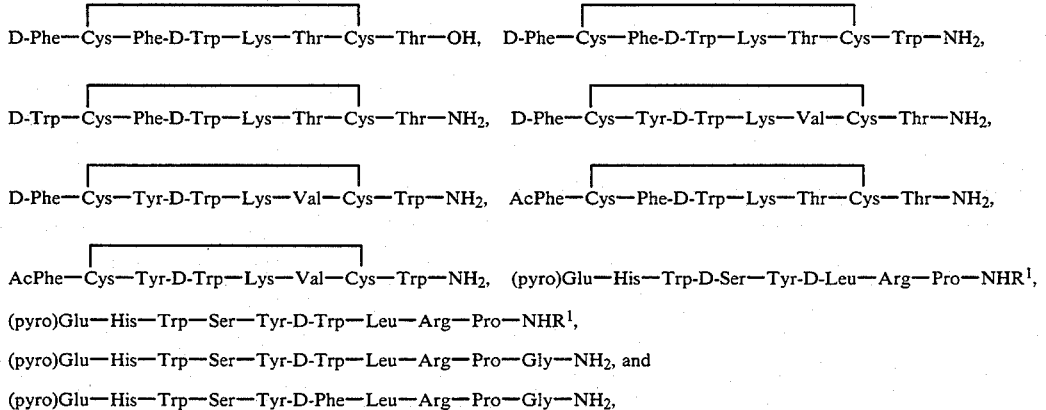

where R$^1$=lower alkyl, this list not being limitative.

The microparticles obtained in accordance with the process of the invention from the above-mentioned ingredients are then used, after an appropriate sterilization, for preparing injectable suspensions.

The following Examples illustrate the invention in more detail, without however being limitative thereof.

EXAMPLE 1

20 g of poly-1,4-butylene succinate, (inherent viscosity of about 0.35 in HFIP) obtained as granules with a diameter ranging approximately from 3 to 5 mm were release of the active substance remains sustained for at least 25 days, as can be inferred from the collapse of the testosterone level to values observed on castrated animals.

EXAMPLE 2

The operations of Example 1 were repeated to obtain microparticles of poly-1,4-butylene succinate (i. v. of about 0.35) containing comparable amounts of the pamoate of one of the following decapeptides:

(pyro)Glu-His-Trp-Ser-Tyr-D-Phe-Leu-Arg-Pro-GlY-NH₂,
(pyro)Glu-His-Trp-D-Ser-Tyr-D-Leu-Leu-Arg-Pro-NR¹, or (pyro)Glu-His-Trp-Ser-Tyr-D-Tyr-Leu-Arg-Pro-NR¹,
where R¹=ethyl.

EXAMPLE 3

The operations of Example 1 were repeated, using as starting material 18 g of poly-1,4-butylene succinate (i. v. of about 0.35) and 2.85 g of the pamoate of an analogue of somatostatin, having the following peptide formula:

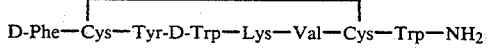

for the preparation of microparticles having the desired particle size.

The chemical analysis carried out on samples of the product after extrusion and milling, confirms the perfect homogeneity of the dispersion of the active substance throughout the bulk of the polymer.

In vivo tests further confirm, that the release of the active substance (an analogue of somatostatin) remains sustained over a period of at least 7 days.

EXAMPLE 4

The operations of Example 3 were repeated, for obtaining microparticles of poly-1,4-butylene succinate with comparable levels of the pamoate of one of the following octapeptides:

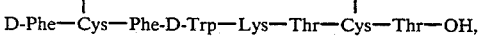

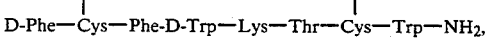

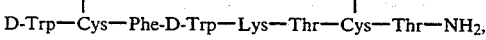

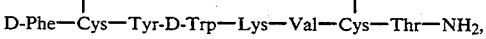

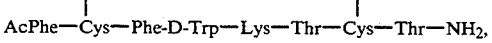

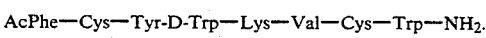

The chemical analysis carried out on samples of the product after extrusion and milling, confirms the perfect homogeneity of the dispersion of the active substance throughout the bulk of the copolymer.

During the experimentation described above, it was found that the extruded filaments, once cut into rods of an appropriate length, can be used directly as implants, after sterilization. Such implants also ensure a sustained and a controlled release of the active substance.

We claim:

1. A process for preparing a pharmaceutical composition designed for the sustained and the controlled release of a drug, including a biodegradable polymer selected from the group consisting of poly-1,4-butylene succinate, poly-2,3-butylene succinate, poly-1,4-butylene fumarate and poly-2,3-butylene fumarate, and incorporating as the active substance the pamoate, tannate, stearate or palmitate salt of a natural or of a synthetic peptide, characterized in that:
   a) the biodegradable polymer and the active substance selected are dry blended, both as microparticles having an average size smaller than about 500 microns;
   b) the powdered mixture is compressed progressively and heated progressively to about 90° C.;
   c) the pre-compressed and pre-heated mixture is subjected to an extrusion at a temperature comprised between about 90° and 100° C., and the extruded product is cooled; and when required:
   d) the product resulting from the extrusion is comminuted at a decreased temperature, and finally the microparticles obtained are selected and collected.

2. A process according to claim 1, characterized in that it includes the steps a, b and c, and in that it leads to the obtention of an implant.

3. A process according to claim 1, characterized in that it includes the steps a, b, c and d and in that it leads to the obtention of microparticles.

4. A process according to claim 3, characterized in that the microparticles of the biodegradable polymer have an average size smaller or equal to 200 microns, and preferably smaller or equal to 180 microns.

5. A process according to claim 1, characterized in that the pre-compression and the pre-heating of the mixture are carried out simultaneously, through the use of one or more endless screws.

6. A process according to claim 1, characterized in that the extrusion is carried out at a pressure comprised between 50 and 500 kg/cm².

7. A process according to claim 1, characterized in that the comminution of the product resulting from the extrusion is a cryogenic comminution.

8. A process according to claim 1, characterized in that the selection of the microparticles resulting from the comminution, is carried out by sieving.

9. A process according to claim 1, characterized in that the active substance is the pamoate, tannate, stearate or palmitate of a natural or of a synthetic peptide comprising 3 to 45 amino acids, and in particular of LH-RH, somatostatin, GH-RH, calcitonin or synthetic peptides.

10. A process according to claim 9, characterized in that the active substance is the pamoate salt of LH-RH, of somatostatin or of one of their synthetic analogues or homologues selected from

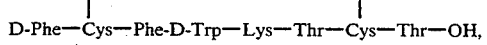 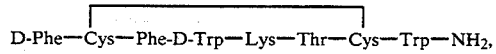

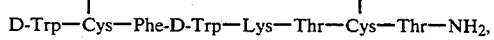 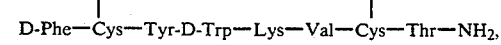

-continued

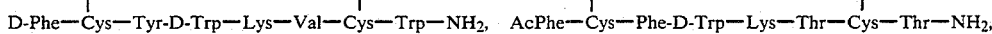
D-Phe—Cys—Tyr-D-Trp—Lys—Val—Cys—Trp—NH₂, AcPhe—Cys—Phe-D-Trp—Lys—Thr—Cys—Thr—NH₂,

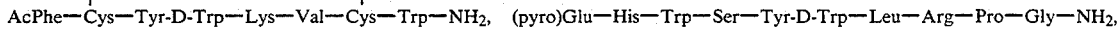
AcPhe—Cys—Tyr-D-Trp—Lys—Val—Cys—Trp—NH₂, (pyro)Glu—His—Trp—Ser—Tyr-D-Trp—Leu—Arg—Pro—Gly—NH₂, (pyro)Glu—His—Trp—Ser—Tyr-D-Phe—Leu—Arg—Pro—Gly—NH₂, (pyro)Glu—His—Trp-D-Ser—Tyr-D-Leu—Leu—Arg—Pro—NHR¹, or (pyro)Glu—His—Trp—Ser—Tyr-D-Trp—Leu—Arg—Pro—NHR¹, where R¹=lower alkyl.

11. The process of claim 1 which further comprises selecting the drug to be present in the polymer at a concentration of between about 0.1 and 15% by weight.

12. A process for preparing a pharmaceutical composition designed for the controlled release of a drug having a natural or synthetic peptide salt as an active substance from a biodegradable polymer comprising polybutylene succinates or fumarates, which comprises:
selecting the drug and polymer to both be in the form of microparticles having an average size of less than about 500 microns;
dry blending the drug and polymer microparticles to form a mixture;
compressing and heating the mixture to about 90° C.;
extruding the compressed and heated mixture at a temperature of between about 90° and 100° C. to form an extruded product; and
comminuting the extruded product at a temperature below 90° C. to obtain microparticles for use as the pharmaceutical composition.

13. The process of claim 12 which further comprises selecting the drug to be present in the polymer at a concentration of between about 0.1 and 15% by weight.

14. The process of claim 12 which further comprises selecting the drug to be in the form of a water insoluble salt.

15. The process of claim 12 which further comprises selecting the drug to be a pamoate, tannate, stearate or palmitate salt of a natural or synthetic peptide having 3 to 45 amino acids.

16. The process of claim 12 wherein the polymer microparticles are initially at a size of less than about 200 microns, and which further comprises extruding the mixture at a pressure between about 50 and 500 kg/cm².

17. The process of claim 12 which further comprises comminuting the extruded product at cryogenic temperatures.

18. The process of claim 12 wherein the selection of the microparticles after comminution is carried out by sieving.

19. The process of claim 12 wherein the compressing and heating of the mixture is carried out simultaneously and progressively by passing the mixture through one or more endless screws.

20. The process of claim 12 which further comprises selecting the peptide to be LH-RH, somatostatin, GH-RH, or calcitonin, or synthetic peptides 21. The process of claim 12 which further comprises selecting the drug to be the pamoate salt of LH-RH, of somatostatin, or of one of their synthetic analogues or homologues selected from the group consisting of:

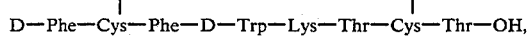
D—Phe—Cys—Phe—D—Trp—Lys—Thr—Cys—Thr—OH,

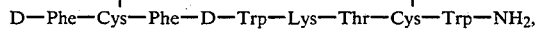
D—Phe—Cys—Phe—D—Trp—Lys—Thr—Cys—Trp—NH₂,

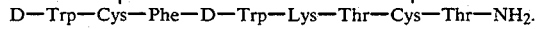
D—Trp—Cys—Phe—D—Trp—Lys—Thr—Cys—Thr—NH₂.

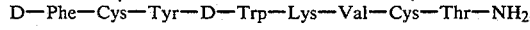
D—Phe—Cys—Tyr—D—Trp—Lys—Val—Cys—Thr—NH₂,

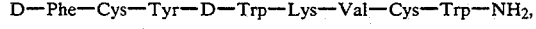
D—Phe—Cys—Tyr—D—Trp—Lys—Val—Cys—Trp—NH₂,

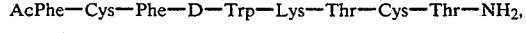
AcPhe—Cys—Phe—D—Trp—Lys—Thr—Cys—Thr—NH₂,

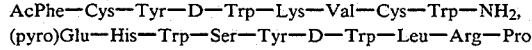
AcPhe—Cys—Tyr—D—Trp—Lys—Val—Cys—Trp—NH₂,
(pyro)Glu—His—Trp—Ser—Tyr—D—Trp—Leu—Arg—Pro—Gly—NH₂,
(pyro)Glu—His—Trp—Ser—Tyr—D—Phe—Leu—Arg—Pro—Gly—NH₂,
(pyro)Glu—His—Trp—D—Ser—Tyr—D—Leu—Leu—Arg—Pro—NHR¹, or
(pyro)Glu—His—Trp—Ser—Tyr—D—Trp—Leu—Arg—Pro—NHR¹, where R¹ consists of a lower alkyl.

22. The process of claim 12 wherein the polymer is selected from the group consisting of poly-1,4-butylene succinate, poly-2,3-butylene fumarate, poly-1,4-butylene fumarate and poly-2,3-butylene succinate.

23. The process of claim 12 wherein the extruded product before comminution comprises the pharmaceutical composition in the form of an implant.

24. A process for preparing a pharmaceutical composition designed for the controlled release of a drug, including a biodegradable polymer comprising polybutylene fumarates or polybutylene succinates, and incorporating as the active substance a pamoate, tannate, stearate or palmitate salt of LH-RH, somatostatin, GH-RH, calcitonin, or synthetic peptides comprising:
  selecting the drug and polymer both to be in the form of microparticles having an average size of less than about 500 microns;
  dry blending the drug and polymer microparticles to form a mixture;
  compressing and heating the mixture to about 90° C.;
  extruding the compressed and heated mixture at a temperature of between about 90° C. and 100° C. to form an extruded product; and
  comminuting the extruded product at a temperature below 90° C. to obtain microparticles for use as the pharmaceutical composition.

* * * * *